United States Patent [19]

Small, Jr. et al.

[11] Patent Number: 5,061,390

[45] Date of Patent: * Oct. 29, 1991

[54] DIETHYLAMINE COMPLEXES OF BORATED ALKYL CATECHOLS AND LUBRICATING OIL COMPOSITIONS CONTAINING THE SAME

[75] Inventors: Vernon R. Small, Jr., Rodeo; Thomas V. Liston, San Rafael; Anatoli Onopchenko, Concord, all of Calif.

[73] Assignee: Chevron Research and Technology Company, San Francisco, Calif.

[*] Notice: The portion of the term of this patent subsequent to Dec. 4, 2007 has been disclaimed.

[21] Appl. No.: 622,878

[22] Filed: Dec. 4, 1990

Related U.S. Application Data

[63] Continuation-in-part of Ser. No. 375,784, Jul. 5, 1989, Pat. No. 4,975,211.

[51] Int. Cl.$^5$ ............................................. C10M 139/00
[52] U.S. Cl. .................................................... 252/49.6
[58] Field of Search ............................................ 252/49.6

[56] References Cited

U.S. PATENT DOCUMENTS

| | | | |
|---|---|---|---|
| 2,344,393 | 3/1944 | Cook et al. | 252/32.7 E |
| 2,497,521 | 2/1950 | Trautman | 252/49.6 |
| 2,785,548 | 6/1957 | Thomas et al. | 252/74 |
| 2,883,412 | 4/1959 | Lowe | 252/49.6 |
| 3,133,800 | 5/1964 | DeGray et al. | 44/69 |
| 3,203,971 | 8/1965 | DeGray et al. | 44/69 |
| 3,361,672 | 1/1968 | Andress et al. | 252/49.6 |
| 3,442,807 | 5/1969 | Law | 252/46.3 |
| 3,445,498 | 5/1969 | Cyba | 260/462 |
| 4,328,113 | 5/1982 | Horodysky et al. | 252/49.6 |
| 4,376,736 | 3/1983 | Stanley | 260/462 R |
| 4,629,577 | 12/1986 | Liston | 252/32.7 E |
| 4,629,578 | 12/1986 | Liston | 252/49.6 |
| 4,632,771 | 12/1986 | Liston | 252/32.7 E |
| 4,643,838 | 2/1987 | Liston et al. | 252/49.6 |
| 4,655,948 | 4/1987 | Doner et al. | 252/49.6 |
| 4,781,850 | 11/1988 | Doner et al. | 252/49.6 |
| 4,975,211 | 12/1990 | Small, Jr. et al. | 252/49.6 |

OTHER PUBLICATIONS

Wilson, J. Chem. Soc., Dalton, pp. 1628–1630 (1973).
Kuremel et al., J. Amer. Chem. Soc., vol. 78, pp. 4572–4575 (1956).
Colclough et al., J. Chem. Soc., pp. 907–911 (1955).
Lohiuis et al., "The Performance of Fuel Saving Engine Oils", SAE/PT-81/22, pp. 261–278.

*Primary Examiner*—Prince Willis, Jr.
*Assistant Examiner*—Jerry D. Johnson
*Attorney, Agent, or Firm*—Richard C. Gaffney

[57] ABSTRACT

Lubricating oils containing a borated alkyl catechol-diethylamine complex are effective in reducing oxidation, wear and deposits in an internal combustion engine.

27 Claims, No Drawings

DIETHYLAMINE COMPLEXES OF BORATED ALKYL CATECHOLS AND LUBRICATING OIL COMPOSITIONS CONTAINING THE SAME

CROSS-REFERENCES TO RELATED APPLICATIONS

This application is a continuation-in-part of U.S. Ser. No. 375,784, filed July 5, 1989, now U.S. Pat. No. 4,975,211.

BACKGROUND OF THE INVENTION

1. Field of the Invention

This invention is concerned with the product obtained by reacting a borated alkyl catechol with diethylamine and the use of said product in lubricant compositions.

2. Description of the Relevant Art

Wear and deposits limit the useful life of automobile and truck engines.

Thus, there is a great need to find lubricants that reduce the oxidation, wear and deposits in the engine, thus increasing the lifetime of the engine.

U.S. Pat. No. 2,795,548 discloses the use of lubricating oil compositions containing a borated alkyl catechol. The oil compositions are useful in the crankcase of an internal combustion engine in order to reduce oxidation of the oil and corrosion of the metal parts of the engine.

There is a problem with the use of borated alkyl catechols in lubricating oils since they are sensitive to moisture and hydrolyze readily. The hydrolysis leads to haze and/or precipitate formation which must be filtered out prior to use. It has now been found that the borated alkyl catechols may be stabilized against hydrolysis by complexing the borated alkyl catechol with diethylamine.

More importantly, it has now been found that lubricating the crankcase of an internal combustion engine with a lubricating oil containing the reaction product of a borated alkyl catechol and diethylamine reduces oxidation and wear in gasoline engines and deposits in diesel engines.

U.S. Pat. No. 2,497,521 to Trautman relates to the use of amine salts of boro-diol complexes in hydrocarbon oil compositions. The amine salts of the boro-diol complexes are useful as stabilizing agents, i.e. antioxidants. The described boro-diol complexes include diols selected from the group consisting of glycols and polyhydroxy benzenes, including catechol. Catechol is a small polar compound which has poor solubility in essentially non-polar base oils under ambient conditions. The use of alkyl catechols to enhance its solubility and compatibility in a base oil is not taught in Trautman. A wide range of amines to prepare the salts is taught; indeed "any organic amine may be employed" (Col. 3, lines 51–71).

A recent patent (U.S. Pat. No. 4,328,113) assigned to Mobil Oil Corporation teaches the use of high molecular weight (C-8+) amines and diamines with boric acid itself for use as grease and lubricating oil additives. The use of borated catechols let alone borated alkylated catechols is not taught in this patent.

U.S. Pat. No. 4,655,948 to Doner et al. discloses grease compositions having increased dropping points. Among the compositions described are mixtures of a hydroxy-containing thickener and borated catechol compounds having the structure:

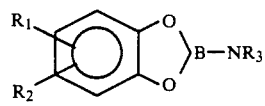

where $R_1$ and $R_2$ are each H or $C_1$ to $C_{40}$; and where $R_3$ is a $C_1$ to $C_{40}$ hydrocarbyl and can contain, additionally, oxygen, sulfur and/or nitrogen-containing moieties.

The catechol amine borate compounds of Doner et al., as indicated in the above formula, are described as trigonal boron compounds having nitrogen-boron single bonds formed by driving the condensation reaction to completion via the azeotropic removal of water. A variety of useful amines are described in Col. 2 lines 62 et seq. Although some amines listed contain secondary amine structures, the common link in all amines is the presence of primary amine structures. It is also to be noted that Donner's list of amines are all high molecular weight aliphatic amines, e.g., oleyl amine or are aromatic, i.e., aniline. Secondary amines, such as diethylamine, are not described.

U.S. Pat. Nos. 3,133,800 and 3,203,971 to De Gray et al. disclose glycol borate amine compounds of aliphatic saturated glycols, useful as fuel additives, for example as deicing agents and bacteriocides. Useful amines, among others, include those with alkyl groups having from 3 to 20 carbon atoms.

U.S. Pat. No. 2,883,412 to Lowe discloses p-xylylene diamine salts of glycol boric acids having superior corrosion inhibiting properties. Among the compounds disclosed are p-xylylene diamine adducts of alkyl catechol borates, such as derived from butyl and cetyl catechol borates (Col. 3 lines 61–68).

Reactions of trialkyl borates with amines, including diethylamine, are described by Wilson in J. Chem. Soc. Dalton, 1973, pp. 1628 and by Colclough et al. in J. Chem. Soc., 1955, pp. 907. The latter, in addition, describes reactions of triphenylborates with amines and on p. 909 shows that attempts to prepare a diethylamine product resulted in a product that was low in amine content. Moreover, even the much more stable pyridine complex of triphenylborate described in this paper hydrolyzed completely in moist air in 5 days. These references do not mention alkyl catechol derivatives.

However, Kuremel et al. in J. Amer. Chem. Soc. 78, pp 4572 (1956) does talk about catechol-boric acid-pyridine complexes. Kuremel shows on p. 4574 that "there is complete dissociation of the complexes into their substituents (pyrocatechol, pyridine, and boric acid) in alcoholic solution". Alkyl catechols were not mentioned.

U.S. Pat. No. 4,629,578 to T. V. Liston teaches that a complex of borated alkyl catechol with a succinimide is useful in lubricant compositions. The succinimide additives of Liston are effective in stabilizing the borated alkyl catechols to hydrolysis. Preferred succinimides have a number average molecular weight of about 600 to about 1,500 (Column 4, lines 12 et seq.). These high molecular weight succinimides effectively dilute the concentration of the desired borated alkyl catechols. In addition, using high molecular weight succinimides for hydrolytic stabilization results in higher transportation costs for the additive, and a loss of flexibility since their use is limited to formulations containing succinimides as dispersants, due to compatibility problems.

Previously, it was believed that low molecular weight amines would not be useful in lubricants subjected to high temperatures, e.g., >100° C. because of the volatility of the amines; that is, it was believed that the amines would be lost during use and not provide ongoing stabilization against hydrolysis. Indeed, all prior art examples show lubricant-type compositions with higher molecular weight amines than diethylamine.

We have now surprisingly found that diethylamine-borated alkyl catechol complexes are stable with respect to decomposition to starting materials under "in use" conditions. The diethylamine stabilized alkyl borated catechols of this invention passed the L-38 engine test (with a score of about 30 mg weight loss), where the presence of "free" amine such as oleyl amine under these conditions would give very high (300-600 mg) weight losses due to corrosion of the copper and lead bearings. Also, calorimetry data (DSC) shows that the diethylamine stabilized alkyl borated catechols of this invention are stable to about 177° C., which is significantly above the sump temperature of a gasoline engine.

The thermal stability of catechol boron amine complexes is not predictable. For example, dimethylamine does not form a stable complex with alkylated borated catechols nor does diisopropyl amine. The interaction of steric effects, nitrogen basicity and boron electrophilicity all come into play. These factors affect the equilibrium between the reactants and the products and make predictions of thermal stability impossible. One also cannot predict hydrolytic stability, which may or may not be related to thermal stability.

The problem, therefore, addressed and solved by this invention is how to hydrolytically stabilize borated alkyl catechols so as to achieve a higher concentration of boron per pound of the borated alkyl catechols. This is achieved by complexing such catechols and stabilizing the same with a low molecular weight stabilizing material, i.e., diethylamine.

SUMMARY OF THE INVENTION

According to the present invention, lubricating oils are provided which reduce wear, oxidation and deposits and are especially useful in the crankcase of internal combustion engines The reduced wear, oxidation and deposits result from the addition to the lubricating oil of small amounts of a complex prepared by reacting a borated alkyl catechol and diethylamine.

Thus, in one aspect, this invention relates to a lubricating oil composition comprising an oil of lubricating viscosity and a minor amount of a hydrolytically stable complex of diethylamine and a borated alkyl catechol.

In another aspect, this invention relates to a concentrate of a neutral carrier oil containing from 5 to 80 weight percent (based on the neutral oil) of the stabilized diethylamine-borated alkyl catechols of this invention.

These complexes may be readily prepared by contacting (a) a borated alkyl catechol and (b) diethylamine under conditions wherein a complex is formed between the diethylamine and the borated alkyl catechol, the amount of said diethylamine being sufficient to stabilize said borated alkyl catechol against hydrolysis.

Other additives may also be present in the lubricating oils in order to obtain a proper balance of properties such as dispersancy, corrosion, wear and oxidation inhibition which are critical for the proper operation of an internal combustion engine.

In still another aspect of this invention, there is provided a method for reducing wear, oxidation and deposits in an internal combustion engine by utilizing the lubricating oil composition described above. Specifically, improvements in deposits of from 10%–50% may be obtained by employing the composition of this invention. This deposit improvement can be obtained in compression-ignition engines, that is, diesel engines. Improvements in viscosity control of 25%–50% can be obtained in spark-ignition engines, that is, gasoline engines. That is, lubricating oil compositions containing the borated alkyl catechol-diethylamine complex of this invention have been found additionally to possess
  (1) antioxidant properties in gasoline engines and
  (2) diesel deposit inhibition when employed in diesel engines.

The borated alkyl catechols may be prepared by borating an alkyl catechol with boric acid with removal of the water of reaction. Typically, there is sufficient boron present such that each boron will react with about 2 to 3 hydroxyl groups present in the reaction mixture. (See Formulas IV, V and VI below.)

The reaction may be carried out at a temperature in the range of 60° C.–135° C. or higher, in the absence or presence of any suitable organic solvent which forms an azeotrope with water such as benzene, xylenes, toluene and the like.

Depending on the ratio of alkyl catechol to boron, the composition of the borated alkyl catechol, and therefore the composition of the amine adduct varies. It is believed that at a 3:2 ratio of alkyl catechol to boron and a 1:1 ratio of boron to nitrogen, the predominant product has a structure like Formula V below. At a 1:1 ratio of alkyl catechol to boron and a 1:1 ratio of boron to nitrogen the predominant product has a structure like Formula VI below.

The alkyl catechols or mixtures thereof which may be used to prepare the borated alkyl catechols used in this invention are preferably mixtures of monoalkyl and dialkyl catechols.

The monoalkyl catechols are preferably of Formula I

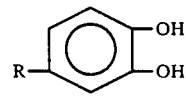

wherein R is alkyl containing at least 10 carbon atoms; usually 10 to 60 carbon atoms and preferably from 18 to 24 carbon atoms and more preferably 20 to 24 carbon atoms. Also, up to 60% by weight but preferably less than 40% by weight of the monoalkyl catechols may have the R group in a position adjacent or ortho to one of the hydroxy groups and have the Formula II

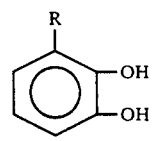

wherein R is as defined above.

The dialkyl catechols which may be used to prepare a mixture of borated alkyl catechols of this invention are generally of Formula III

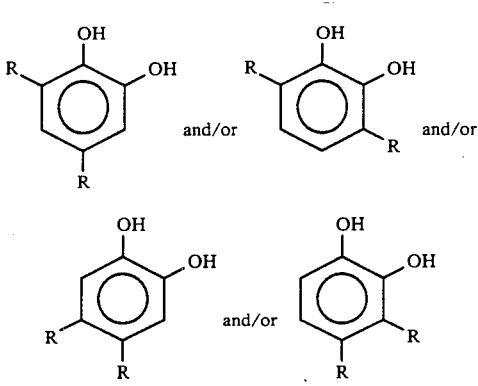

wherein R is as defined above and the two R groups can be the same or different. Trialkyl catechols may also be employed although they are not preferred.

As noted above, the alkyl group on the alkyl-catechol contains at least 10 carbon atoms. Suitably the alkyl group can have from 10 to 60 carbon atoms or more and, of course, mixtures of such alkyl groups can be employed.

Among the alkyl catechols which may be employed are decyl catechol, undecyl catechol, dodecyl catechol, tetradecyl catechol, pentadecyl catechol, hexadecyl catechol, octadecyl catechol, eicosyl catechol, hexacosyl catechol, triacontyl catechol, tetracontyl catechol, pentacontyl catechol, hexcontyl catechol and the like. Also, a mixture of alkyl catechols may be employed such as a mixture of $C_{14}$–$C_{18}$ alkyl catechols, a mixture of $C_{18}$–$C_{24}$ alkyl catechols, a mixture of $C_{20}$–$C_{24}$ alkyl catechols, a mixture of $C_{16}$–$C_{26}$ alkyl catechols or a mixture of $C_{32}$–$C_{60}$ alkylcatechols.

For the higher carbon number alkyl groups, such as those having greater than 30 carbon atoms, e.g., from 32 to 60 carbon atoms, preferably 36 to 50 carbon atoms, such alkyl groups are preferably derived from "alpha olefin oligomer(s)".

The term "alpha olefin oligomer" as used herein refers to alpha olefin dimers, trimers, tetramers and pentamers or mixtures which have, in total, from 32 to 60 carbon atoms. Such alpha olefin oligomers can be prepared or derived from $C_8$ to $C_{20}$ alpha olefins, preferably $C_{10}$–$C_{14}$ alpha olefins, or mixtures. Examples of alpha olefin oligomers include $C_8$ tetramers and pentamers; $C_{10}$ tetramers and pentamers; $C_{12}$ trimers and tetramers; $C_{14}$ trimers; $C_{16}$ dimers and trimers; $C_{18}$ dimers; and $C_{20}$ dimers. For higher carbon number alkyl groups, i.e., those having greater than 30 C's, the further preferred alkyl groups are those having a number average carbon number from 35 to 45. Such higher carbon number alkyl groups can be single carbon number alkyl groups such as an alkyl group prepared using a tetramer of decene-1. Usually, such higher carbon number alkyl groups are a mixture of dimers, trimers, tetramers, etc., (collectively oligomers) of alpha- olefins having from 8 to 20 carbon atoms per molecule, so long as the number average carbon number of the mixture is from 35 to 45. For example, a mixture of alpha olefin oligomers containing 10% by weight $C_{30}$, 50% by weight $C_{40}$ and 40% by weight $C_{50}$ oligomers has a number average carbon number of 43 i.e. $(30 \times 0.10)+(40 \times 0.50)+(50 \times 0.40)=43$.

The alpha olefin oligomers used herein are prepared by methods well-known in the art. For example, these oligomers can be prepared using boron trifluoride catalysts as described in U.S. Pat. Nos. 4,238,343 and 4,045,507, and in Onopchenko, et al, *BF$_3$-Catalyzed Oligomerization of Alkenes* (*Structures, Mechanisms and Properties*), 183rd ACS Natl. Meet: (Las Vegas, March 1982), *Ind. Eng. Chem., Prod. Res. Dev.*, 22(2), 182–91 (June 1983).

The alkyl catechols useful in this invention may be prepared by reacting an alpha-olefin having at least 10 carbon atoms, such as a branched olefin or straight-chain alpha olefin containing at least 10 carbon atoms or mixtures with catechol in the presence of a sulfonic acid catalyst at a temperature of from about 60° C.–200° C., preferably 125° C.–180° C., and most preferably 130° C.–150° C. in an essentially inert solvent at atmospheric pressure. Although alkylation of catechol can be carried out neat, in absence of solvents, the use of solvents, particularly in a batch reactor greatly facilitates the process due to better contact of the reactants, improved filtration, etc. Examples of the inert solvents include benzene, toluene, chlorobenzene and Chevron 250 Thinner which is a mixture of aromatics, paraffins and naphthenes.

The term "branched olefin" means that branching occurs at the double bond, i.e., vinylidene olefins or trisubstituted olefins. The term "straight-chain alpha olefin" means that the alpha olefin contains little (less than about 20%) or no branching at the double bond or elsewhere.

Monoalkyl catechols are preferred. A product which is predominantly monoalkyl catechol may be prepared by using molar ratios of reactants (catechol and alkylating olefin) and preferably a 10% molar excess of branched olefin or alpha olefin over catechol is used. When used at molar ratios, the resulting products are generally predominantly monoalkyl catechols but do contain some amounts of dialkyl catechol A molar excess of catechol (e.g. two equivalents of catechol for each equivalent of olefin) can be used in order to enhance monoalkylation if predominantly monoalkyl catechol is desired. Predominantly dialkyl catechols may be prepared by employing a molar excess of olefin, such as two equivalents of the same or different olefin per equivalent of catechol.

Dialkyl catechols are also useful in this invention. A typical weight ratio of monoalkyl to dialkyl catechol is in the range of 1:3 to 3:1.

Use of a branched olefin results in a greater proportion of alkyl catechols of Formula I than use of straight-chain alpha olefins. Use of such branched olefins generally results in greater than 90% alkyl catechol of Formula I and less than 10% alkyl catechol of Formula II. On the other hand, the use of a straight-chain alpha olefin generally results in approximately 50% of alkyl catechols of Formula I and 50% of Formula II. In a case of $C_{20}$–$C_{24}$ olefin mixture, for example, containing 20% branching, the corresponding alkyl catechols will comprise about 60% of Formula I and 40% of Formula II. When the same or different olefin mixture contains 50% branching, the corresponding alkyl catechols will comprise approximately 70% of Formula I and 30% of Formula II.

The exact structure of the complex of this invention is not known for certain. However, while not limiting this invention to any theory, it is believed that the compounds of this invention have a tetrahedral boron atom with three B—O bonds. The boron is either complexed to the nitrogen atom in the diethylamine via dative bonding, or is present as a salt.

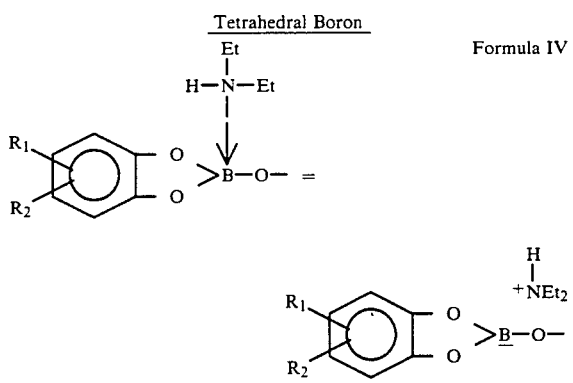

Formula IV illustrates dative bonding.

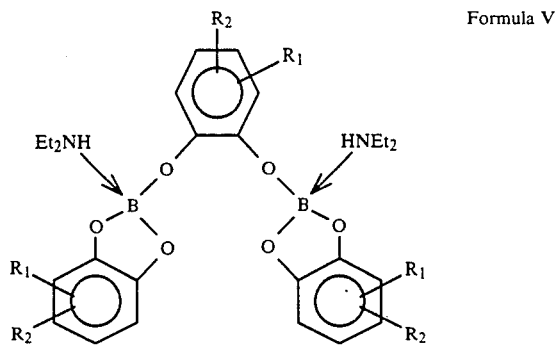

Formula V is a 3:2 catechol to boron complex.

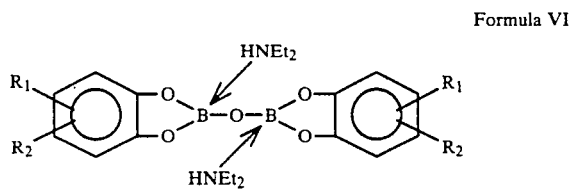

Formula VI is a 1:1 catechol to boron complex.

A borated alkyl catechol having a 3:2 mole ratio of catechol to boron (Formula V) or a 1:1 mole ratio of catechol to boron (Formula VI) is a function of the mole ratio of catechol to boron as noted above. The only two products that are believed to be present are the 1:1 and 3:2 products of Formulas V and VI. Nevertheless, due to equilibrium considerations, the product most likely is a mixture of the 1:1 and 3:2 complexes in varying proportions depending on the stoichiometry used. We have found that a 3:2 product is just as effective in a Sequence IIID test as the 1:1 product. It is thus preferred for cost and handling reasons that the borated alkyl catechol predominate in the 3:2 product and, more preferably, be substantially only the 3:2 product, i.e., that the product be made using a mole ratio of alkyl catechol to boron of about 3:2.

The complex may be formed by reacting the borated alkyl catechol and the diethylamine together neat at a temperature above the melting point of the mixture of reactants and below the decomposition temperature, or at a suitable temperature in a diluent in which both reactants are soluble. Suitable temperatures can be about 30° C. to 100° C., preferably about 50° C. For example, the reactants may be combined in the proper ratio in the absence of a solvent to form an homogeneous product or the reactants may be combined in the proper ratio in a solvent such as toluene or benzene, xylenes, chlorobenzene, or thinner, and the solvent then stripped off. The complex formed by either technique may then be added to the oil. Most diethylamine complexes of borated alkyl catechols are either liquids at room temperature, or low melting solids (m.p. 30° C.–40° C.) depending on the composition of their isomers and the purity of the product. Alternatively, the complex may be prepared in a lubricating oil as a concentrate containing from about 5 to 80% by weight of the complex, which concentrate may be added in appropriate amounts to the lubricating oil in which it is to be used or the complex may be prepared directly in the lubricating oil in which it is to be used.

The diluent is preferably inert to the reactants and products formed, and is used in an amount sufficient to ensure solubility of the reactants and to enable the mixture to be efficiently stirred.

Temperatures for preparing the complex may be in the range of from 20° C.–200° C. and preferably 25° C.–60° C. and under sufficient pressure to maintain the diethylamine in the liquid phase. The most preferred temperatures depend on whether the complex is prepared neat or in a diluent, i.e., higher temperatures may be used when a solvent is employed.

An effective amount of diethylamine is added in order to stabilize the borated alkyl catechols against hydrolysis. In general, mole ratios of diethylamine to boron used to form the complex are in the range of 0.8:1 to 1.1:1, and preferably from 0.9:1 to 1:1, and most preferably 1:1. This latter ratio is preferred if the complex is made and/or stored neat or in the absence of solvent or lubricating oil and under atmospheric conditions. Higher amounts of the diethylamine can be used but provide no advantages. However, normally excess amine is added to insure complete stabilization and unreacted amine is recovered and recycled.

As used herein, the term "stabilized against hydrolysis" means that the borated alkyl catechol-diethylamine complex does not "skin-over" or form a precipitate due to the hydrolysis of the borated catechol for a period of at least one week, preferably three months, when stored at room temperature (~15°–25° C.) and ambient humidity, i.e., no observable or measurable free boric acid is formed. By a stabilizing amount of amine is meant that amount to stabilize the borated alkyl catechol against hydrolysis.

The amount of the complex required to be effective for reducing wear, oxidation and deposits in lubricating oil compositions is a minor amount and may range from 0.05% to 20% by weight. However, in the preferred embodiment, it is desirable to add sufficient complex so that the amount of borated catechol is added at a range from 0.1% to about 4% by weight of the total lubricant composition and preferably is present in the range from 0.2% to 2% by weight and most preferably 0.5% to 1%.

The diethylamine is present in the complex of the invention in an amount effective to stabilize the borated alkyl catechol against hydrolysis and which allows the borated alkyl catechol to function as an effective oxidation and deposit reducing agent.

The diethylamine-borated alkyl catechol complexes of this invention can be added to a lubricating oil (or can be made in the lubricating oil). In addition, it is contemplated that the complexes of this invention can be sold as a concentrate in a neutral oil with or without other ingredients such as dispersants, antirust agents, etc. The concentrate can therefore comprise a complex of a borated alkyl catechol and an amount to hydrolytically stabilize the borated alkyl catechol of diethylamine plus a neutral carrier oil. The weight percent of the diethylamine stabilized borated alkyl catechol in the concentrate is usually from 5 to 80 based on the weight of neutral carrier oil, typically 10 to 60. The term "neutral oil" is well known in the art, such as those neutral oils made commercially which have a viscosity in the lubricating oil range, such as 100 neutral oils, 200 neutral oils, etc.

In general, the complexes of this invention may also be used in combination with other additive agents in conventional amounts for their known purpose. For example, for application in modern crankcase lubricants, the base composition described above will be formulated with supplementary additives to provide the necessary stability, detergency, dispersancy, antiwear and anticorrosion properties.

Thus, as another embodiment of this invention, the lubricating oils which contain the complexes prepared by reacting the borated alkyl catechols and diethylamine may also contain an alkali or alkaline earth metal hydrocarbyl sulfonate, an alkali or alkaline earth metal phenate, and Group II metal salt dihydrocarbyl dithiophosphate, and conventional viscosity index improvers.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and the forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 mg of KOH per gram of sample or more. Carbon dioxide and calcium hydroxide or oxide are the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposit of contaminants formed during high temperature operation of the engine. The phenols may be mono- or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, triacontyl, and the like. Other suitable synthetic sources of the alkyl radical include olefin polymers such as polypropylene, polybutylene, polyisobutylene and the like.

The alkyl group of the alkyl phenate can be straight-chained or branched-chained, saturated or unsaturated (if unsaturated, preferably containing not more than 2 and generally not more than 1 site of olefinic unsaturation). The alkyl radicals will generally contain from 4 to 30 carbon atoms. Generally, when the phenol is monoalkyl-substituted, the alkyl radical should contain at least 8 carbon atoms. The phenate may be sulfurized if desired. It may be either neutral or overbased and if overbased will have a base number of up to 200 to 300 mg of KOH per gram of sample or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2% to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently, the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al., U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, Columns 6 and 7, wherein these compounds and their preparation are described generally. Suitably, the Group II metal salts of the dihydrocarbyl dithiophosphoric acids useful in the lubricating oil composition of this invention contain from about 4 to about 18 carbon atoms in each of the hydrocarbyl radicals and may be the same or different and my be aromatic, alkyl or cyclo-alkyl. Preferred hydrocarbyl groups are alkyl groups containing from 4 to 8 carbon atoms and are represented by butyl, isobutyl, sec-butyl, hexyl, isohexyl, octyl, 2-ethylhexyl, p-tolyl, xylyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

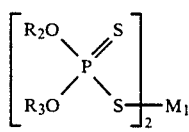

wherein:
$R_2$ and $R_3$ each independently represent hydrocarbyl radicals as described above, and
$M_1$ represents a Group II metal cation as described above.

The dithiophosphoric salt is present in the lubricating oil compositions of this invention in an amount effective to inhibit wear and oxidation of the lubricating oil. The amount ranges from about 0.1% to about 4% by weight of the total composition, preferably the salt is present in an amount ranging from about 0.2% to about 2.5% by weight of the total lubricating oil composition. The final lubricating oil composition will ordinarily contain 0.025% to 0.25% by weight phosphorus and preferably 0.05% to 0.15% by weight. The finished lubricating oil may be single or multigrade. Multigrade lubricating oils are prepared by adding viscosity index (VI) improvers. Typical viscosity index improvers are polyalkyl methacrylates, ethylene propylene copolymers, styrene-diene copolymers and the like. So-called decorated VI improvers having both viscosity index and dispersant properties are also suitable for use in the formulations of this invention.

The lubricating oil used in the compositions of this invention may be mineral oil or synthetic oils of lubricating viscosity and preferably suitable for use in the crankcase of an internal combustion engine. Crankcase lubricating oils ordinarily have a viscosity of about 1300 cSt at 0° F. to 22.7 cSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$-$C_{12}$ alpha olefins such as 1-decene trimer. Likewise, alkyl benzenes of proper viscosity, such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono- and dicarboxylic acid and mono- and dihydroxy alkanols can also be used. Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Other additives which may be present in the formulation (or in the concentrate referred to above) include rust inhibitors, foam inhibitors, corrosion inhibitors, metal deactivators, pour point depressants, antioxidants, and a variety of other well-known additives.

The following examples are offered to specifically illustrate the invention. These examples and illustrations are not to be construed in any way as limiting the scope of the invention.

EXAMPLES

Example 1

Preparation of $C_{18}$–$C_{24}$ Alkyl Catechol by Batch Process

A 30-gallon reactor equipped with a stirrer, condenser, Dean-Stark trap, and nitrogen inlet and outlet, was charged with 61.67 pounds of $C_{18}$-$C_{24}$ olefins (less than $C_{14}$, 2.7%; $C_{14}$, 0.3%; $C_{16}$, 1.3%; $C_{18}$, 8.0%; $C_{20}$, 44.4%; $C_{22}$, 29.3%; $C_{24}$, 11.2%; $C_{26}$ and above, 2.8%) containing at least 40% branched olefins (available from Ethyl Corp.), 18.32 pounds catechol, 8.0 pounds sulfonic acid cation exchange resin (polystyrene cross-linked with divinylbenzene) catalyst (Amberlyst-15, available from Rohm and Haas, Philadelphia, Pa.), and 9 gallons of Chevron 350H thinner. With a stirrer set at 150 rpm, the reaction was carried out at 141° C.-143° C. for a total of 14.7 hours. The reaction mixture was stripped by heating at 143° C. under vacuum (50 mm Hg) for 4 hours. The product was filtered hot over diatomaceous earth to afford 67.21 pounds of a liquid $C_{18}$–$C_{24}$ alkyl catechol. The product contained 1.4% of unreacted catechol by infrared analysis, a hydroxyl number of 199 mg KOH/g, and a low sediment level of 0.02 vol %. Chromatographic analysis showed the product to contain 2.6% of Chevron 350H thinner, 7.4% unreacted olefin, 45.2% monoalkyl catechols, and 44.8% dialkyl catechols.

EXAMPLE 2

Preparation of $C_{20}$-$C_{24}$ Alkyl Catechol by Batch Process

A 10-gallon reactor equipped with a stirrer, condenser, Dean-Stark trap, and nitrogen inlet and outlet, was charged with 15.68 pounds of a mixture of $C_{20}$-$C_{24}$ olefins ($C_{18}$, 2.2%; $C_{20}$, 47.3%; $C_{22}$, 39.8%; $C_{24}$, 10.2%; $C_{26}$, 0.5%) containing at most 20% branched olefins (available from Chevron), 4.76 pounds catechol, 2.16 pounds sulfonic acid cation exchange resin (polystyrene cross-linked with divinylbenzene) catalyst (Amberlyst-15, available from Rohm and Haas, Philadelphia, Pa.), and 1.5 gallons of Chevron 350H thinner. The reaction mixture was heated at 135° C.-143° C. for a total of 14 hours, with a stirrer set at 200 rpm under a nitrogen atmosphere. The reaction mixture was then stripped by heating at 150° C. under vacuum (25 mm Hg) for two hours. The product was filtered hot over diatomaceous earth to afford 16.83 pounds of a liquid $C_{20}$-$C_{24}$ alkyl catechol. The product contained 1.7% of unreacted catechol by infrared analysis, a hydroxyl number of 195 mm KOH/g, and a low sediment level of 0.02 vol %. Chromatographic analysis showed the product to contain 3.3% of Chevron 350H thinner, 3.4% unreacted olefin, 42.9% monoalkyl catechols, and 50.4% dialkyl catechols.

EXAMPLE 3

Preparation of $C_{18}$-$C_{24}$ Alkyl Catechol by Continuous Flow Reactor

A 450-ml mixture of catechol and $C_{18}$-$C_{24}$ olefin (same as in Example 1 above), in a molar ratio of 0.90/1.0, was preheated to 120° C. in a volumetric burette, and then pumped upward through a 24-inch × ½-inch O.D. stainless steel reactor containing 210 ml of Amberlyst-15, maintained at 120° C. (±2°), over a period of 7 hours. The extent of reaction was monitored by GLC. The product was collected and recycled 5 times until the reaction was essentially complete. Analysis of final product by GLC after a total of 40 hours onstream showed the following composition: catechol, 3.3%; unreacted olefin and paraffin present in olefin feed, 14.6%; monoalkyl catechols, 54.3%; and dialkyl catechols, 27.8%. The linear hourly space velocity (LHSV) corresponded on the average to about 0.30 per hour (i.e., volume feed/volume catalyst/hour). The weight ratio of monoalkyl- to dialkyl catechols in the product corresponded to about 66:34.

EXAMPLE 4

Boration of $C_{18}$-$C_{24}$ Alkyl Catechol

A 3-liter, three-necked, round-bottomed glass flask, equipped with a stirrer, condenser, Dean-Stark trap, and nitrogen inlet, was charged with 860 g of $C_{18}$-$C_{24}$ alkyl catechols prepared according to Example 1, 79.1 g boric acid, and 1200 ml toluene. The reaction mixture was heated under reflux, while stirring, at 115° C.-125° C., collecting a total of 50 g of water in the trap in 6 hours. The reaction mixture was then stripped of solvent by heating at 135° C. under vacuum (20-25 mm Hg) for 3 hours to give 850 g of a liquid, borated $C_{18}$-$C_{24}$ alkyl catechol. Analysis for boron gave a value of 1.3%, and a measured viscosity at 100° C. of 27 cSt. Exposure of a small sample of product to atmospheric moisture, resulted in boric acid formation on the surface in a matter of seconds. In less than one day the material was hazy and crusted on top. This product was prepared using 3 moles of catechol per 2 moles of boron and the product is believed to have the structure shown in Formula V above.

EXAMPLE 5

Boration of $C_{20}$-$C_{24}$ Alkyl Catechol

A 2-liter, three-necked, round-bottomed flask, equipped with a stirrer, condenser, Dean-Stark trap, and nitrogen inlet, was charged with 585 g of $C_{20}$-$C_{24}$ alkyl catechol prepared according to Example 2, 41.1 g boric acid, and 785 ml toluene. The mixture was then heated while stirring at reflux (115° C.-125° C.) under nitrogen for a period of 6 hours, collecting a total of 32 g of water in the Dean-Stark trap, although most of the water had been collected during the first 3 hours. The product was then stripped of toluene solvent by heating the reaction mixture to 135° C. under vacuum (20-25 mm Hg) for 3.5 hours. A total of 580 g of borated $C_{20}$-$C_{24}$ alkyl catechol was isolated, which partially solidified on standing in the flask, under nitrogen, at room temperature. The product had a measured viscosity at 100° C. of 30 cSt, and boron content of 1.28%. Exposure of a small sample of product to atmospheric moisture on a watch glass, led to formation of white, crystalline, boric acid on the surface in a matter of seconds. This product was prepared using 3 moles of catechol per 2 moles of boron and the product is believed to have the structure shown in Formula V above.

EXAMPLE 6

Amine Treatment of Borated $C_{18}$-$C_{24}$ Alkyl Catechol

A 2-liter, three-necked, round-bottomed glass flask, equipped with a stirrer, condenser, and an addition funnel, was charged with 770 g of borated $C_{18}$-$C_{24}$ alkyl catechol prepared according to Example 4. While vigorously stirring, 88 g of diethylamine was added to the alkyl catechol over a period of 1 hour, maintaining a temperature during addition below 50° C. When amine addition was completed, the reaction mixture was stirred at 50° C. for 1 hour, and then heated to 135° C. under vacuum (20-25 mm Hg) for 1 hour to remove unreacted amine. A total of 821 g of product was recovered, containing 1.27% of boron, which gave a measured viscosity at 100° C. of 280 cSt. The product on exposure to atmospheric moisture gave no evidence of boric acid formation after 1 hour and after one year, the product remained bright and clear.

Comparing Examples 4 and 6, it can be seen that the haze and crust formed in Example 4 can be prevented by using an effective amount of diethylamine.

The addition of the diethylamine results in a substantial viscosity increase in the final complex but this increase in viscosity is quite manageable in the plant for manufacturing purposes. Usually, the viscosity of the complex is typically in the range of 200 to 400 cSt at 100° C.

EXAMPLE 7

Amine Treatment of Borated $C_{20}$-$C_{24}$ Alkyl Catechol

A 100-g sample of product prepared according to Example 5 was dissolved in about 100 ml of toluene, and while stirring, was treated with 10.2 g of diethylamine over a period of about 10 minutes, allowing the temperature of the reaction to reach 52° C. After about 15 minutes, when the temperature started to decrease, the mixture was heated to 135° C. under vacuum (20-25 mm Hg) for 1.5 hours, to strip off unreacted amine and the solvent. A total of 98.3 g of product was isolated as an oil, which on standing solidified to a low melting solid, m.p. 35° C. Analysis for boron and nitrogen gave values of 1.20% and 1.09%, respectively. The product had a measured viscosity at 100° C. of 300 cSt. The product on exposure to atmospheric moisture for about 1 hour showed no signs of any hydrolysis and this remained true even after three months.

EXAMPLE 8

Boration and Amine Treatment of $C_{18}$-$C_{24}$ Alkyl Catechol in Large Vessel A 30-gallon reactor equipped with a stirrer, condenser, and Dean-Stark trap, was charged with 44.05 pounds of $C_{18}$–$C_{24}$ alkyl catechol prepared according to Example 1, 4.25 pounds boric acid, and 5.8 gallons Chevron 51 L solvent. The reaction mixture was heated while stirring at 150 rpm at reflux (100° C.–124° C.) for a total of 22 hours, collecting 3.08 pounds of water in the trap. The reaction mixture was cooled to room temperature, and while stirring, 5.03 pounds of diethylamine was incrementally added to the reaction mixture over a period of 4 hours, maintaining a temperature during addition below the boiling point of the amine (55° C.). When amine addition was completed, the reaction mixture was heated to 100° C. for 1 hour, and then stripped at 100° C. under vacuum (45–50 mm Hg) for 1 hour, and finally 135° C. for an additional hour. A total of 52.20 pounds of borated and diethylamine treated $C_{18}$–$C_{24}$ alkyl catechol was formed. The product gave a total base number (TBN) of 45 mg KOH/g, and a sediment value of 0.08 vol %. Analysis for boron and nitrogen gave values of 1.15% and 1.20%, respectively. The product on exposure to atmospheric moisture for about 1 hour showed no signs of any hydrolysis and this remained true even after three months. This product was prepared using 3 moles of catechol per 2 moles of boron and the product is believed to have the structure shown in Formula V above.

EXAMPLE 9

Boration and Amine Treatment of $C_{20}$–$C_{24}$ Alkyl Catechol

A 3-liter, round-bottomed flask, equipped with a condenser, stirrer, Dean-Stark trap, and an additional funnel, was charged with 4.40 pounds of $C_{20}$–$C_{24}$ alkyl catechol prepared according to Example 2, 0.63 pounds boric acid, and approximately 0.30 gallons toluene. The mixture was heated under reflux, while stirring, collecting a total of 0.29 pounds of water in a course of 4 hours. The borated alkyl catechol in toluene in the flask was cooled to room temperature, and gradually treated with 0.78 pounds diethylamine over a period of 4 hours, maintaining a temperature during addition below the boiling point of diethylamine (55° C.). After standing overnight, the reaction mixture was stripped at 140° C. under high vacuum (2–3 mm Hg) for 3 hours to give 4.62 pounds of liquid, borated, amine treated $C_{20}$–$C_{24}$ alkyl catechol. On standing, the product solidified to a low melting material, m.p. 33° C. Analysis for boron and nitrogen gave values of 1.10% and 1.09%, respectively.

Measurement of viscosity at 100° C. gave a value of 325 cSt. Analysis of product by differential scan calorimetry (DSC) gave an exotherm at 177° C., suggesting that the loss of amine had occurred at this temperature. The product on exposure to atmospheric moisture for about 1 hour showed no signs of any hydrolysis and this remained true even after 3 months. This product was prepared using 3 moles of catechol per 2 moles of boron and the product is believed to have the structure shown in Formula V above.

Gasoline Engine Runs

A series of Examples were carried out which demonstrate the improvements in oxidation and wear obtained by adding lubricating oil compositions of this invention to the crankcase of a gasoline automobile engine using additives prepared by Example 6.

In these Examples, a 350 CID Oldsmobile gasoline engine was run on a dynamometer. An engine oiling system was devised in order to provide proper lubrication to the engine and also to provide the capability to change the oil without stopping the engine. Basically, a dry sump system was used with an external pump providing lubrication to the engine. This pump was connected through valves to four external sumps. The positioning of the valves determined the oil used. The gasoline engine runs were carried out in an eight-cylinder Oldsmobile engine for a period of 64 hours according to Sequence IIID specifications. The formulation contained a known concentration of oxidation inhibitor of this invention to be tested, 3.5% dispersant, 40 mmol/kg mixed calcium and magnesium sulfonates, 16 mmol/kg mixed zinc dialkyldithiophosphates, 10% viscosity index improver (ethylene propylene copolymer) in Exxon 100N/150N base oils, formulated to SAE 10W-30 grade. The reference runs (Examples 10 and 11 below) were carried out under identical conditions, using the same stand, using the above formulation, but containing no oxidation inhibitor, i.e., without using the stabilized borated alkyl catechols of this invention. The results of the Examples are summarized in Table I below.

TABLE I

SEQUENCE IIID ENGINE TEST RESULTS IN EXXON BASE OIL

| Example Number | Additive | Additive Conc., Wt. % | | Hours to 375% Viscosity Increase | | Average Cam & Lifter Wear, mils |
|---|---|---|---|---|---|---|
| 10 | None | (reference) | | 32.6 | | 0.9 |
| 11 | None | (reference) | | 26.6 | | 0.9 |
| | | | avg | 29.6 | (4.2)* | 0.9 (0)² |
| 12 | Example 6¹ | 1.1 | | 56.8 | | 0.7 |
| 13 | Example 6¹ | 1.1 | | 56.9 | | 1.4 |
| | | | avg | 56.9 | (0.1) | 1.1 (0.5) |
| 14 | Example 6¹ | 2.2 | | 110.0 | | 1.1 |
| 15 | Example 6¹ | 2.2 | | 82.0 | | 1.0 |
| | | | avg | 96.0 | (20) | 1.0 (0.1) |

¹The additive was as prepared in Example 6 above.
²Standard deviation.

Referring to Table I, the reference runs (Examples 10 and 11) showed 29.6 hours to increase viscosity 375%. The Sequence IIID specification is a minimum of 64 hours to have a 375% increase in viscosity. Similarly, Sequence IIID specifies a wear of less than 4.0 mils. A comparison of Examples 12 through 15 with Examples 10 and 11 shows the improvements in antioxidant properties by the addition of the additives of the invention.

Other engine Examples were carried out in Chevron base oils employing the formulation consisting of a known concentration of oxidation inhibitor, 3.5 wt. % dispersant, 45 mmol/kg mixed calcium and magnesium sulfonate, 13 mmol/kg zinc dialkyldithiophosphate, 10.5% viscosity index improver (ethylene propylene copolymer) in Chevron base oils formulated to a 5W-30 grade. The results are summarized in Table II below.

TABLE II
SEQUENCE IIID ENGINE TEST RESULTS IN CHEVRON BASE OIL

| Example Number | Additive | Additive Conc., Wt. % | Hours to 375% Viscosity Increase | Average Cam & Lifter Wear, mils |
|---|---|---|---|---|
| 16 | None | (reference) | 24.2 | 3.3 |
| 17 | None | (reference) | 30.7 | 1.4 |
| | | | avg 27.5 (4.6)* | 2.4 (1.3)[2] |
| 18 | Example 6[1] | 0.55 | 32.1 | 2.1 |
| 19 | Example 6[1] | 0.55 | 43.1 | 2.2 |
| | | | avg 37.6 (7.8) | 2.2 (0.1) |
| 20 | Example 6[1] | 1.1 | 56.0 | 2.1 |
| 21 | Example 6[1] | 1.1 | 50.5 | 5.7 |
| | | | avg 53.3 (3.9) | 3.9 (2.5) |

[1]The additive was as prepared in Example 6 above.
[2]Standard deviation.

Referring to Table II, a comparison of Examples 18 through 21 with the base runs (Examples 16 and 17) shows that the addition of the stabilized borated alkyl catechols of the invention improves the oxidation properties of the Chevron base oils.

Diesel Engine Examples

A series of Examples were carried out which demonstrate the improvements in deposit control in a diesel engine by adding additives prepared according to Example 8 or 9.

The diesel engine runs were carried out in a single cylinder Caterpillar engine for a period of 60 hours according to 1G2 specification, using a formulation containing a diesel deposit inhibitor of Example 8, 8% dispersant, 50 mmol/kg calcium phenate, 16 mmol/kg mixed zinc dialkyldithiophosphate, and 10% viscosity index improver (ethylene propylene copolymer) in Chevron 100N/240N base oil. For comparison purposes, the reference runs were carried out under identical conditions, in the same engine stand, using the above formulation, but without the deposit inhibitor. The results are shown in Table III.

TABLE III
1G2 DIESEL ENGINE TEST RESULTS

| Example Number | Additive | Additive Conc., wt % | TGF[1] | WTD[2] |
|---|---|---|---|---|
| 22 | None | Reference | 86 | 528 |
| 23 | None | Reference | 81 | 383 |
| 24 | None | Reference | 69 | 340 |
| 25 | None | Reference | 74 | 524 |
| 26 | None | Reference | 74 | 378 |
| 27 | None | Reference | 58 | 359 |
| | | | avg 74 (10)* | 419 (85)* |
| 28 | Example 8 | 2.2 | 62 | 428 |
| 29 | Example 8 | 2.2 | 56 | 244 |
| 30 | Example 9 | 2.2 | 77 | 423 |
| 31 | Example 9 | 2.2 | 57 | 283 |
| | | | avg 61 (10) | 344 (95) |

*Standard deviation.
[1]TGF = top groove fill.
[2]WTD = weighted total demerits.

Referring to Table III, six reference runs (Examples 22–27) were made to obtain a statistically meaningful base average for TGF and WTP.

A comparison of Examples 28–31 with the average of Examples 22–27 shows that using the stabilized alkyl borated catechol of this invention improves the deposit control properties of the lubricating oil.

EXAMPLES 32–34

In these Examples, three different amines were used to stabilize a borated alkyl catechol (as prepared in Example 4 above) and wherein the catechol to boron mole ratio was 3:2. The amount of amine added was sufficient to achieve a 1:1 nitrogen to boron mole ratio. The results are shown in Table IV below.

TABLE IV
Dialkylamine Stabilized Borates

| Example | Amine | Borate C:B[1] | Hydrolytic Stability Rating[2] |
|---|---|---|---|
| 32 | Dimethyl | 3:2 | 1 |
| 33 | Diethyl | 3:2 | 6 |
| 34 | Diisopropyl | 3:2 | 3 |

[1]Catechol to Boron mole ratio in preparing borate.
[2]1 = Extensive, immediate hydrolysis.
2 = Some immediate hydrolysis.
3 = Hydrolysis within one day.
4 = Hydrolysis within one to three days.
5 = Hydrolysis within three to seven days.
6 = Stable to atmospheric moisture for at least seven days. Example 33 was stable for more than 6 months.

As can be seen from Table IV, only diethylamine provides acceptable hydrolytic stability.

EXAMPLES 35–38

In these Examples, three different amines were used to stabilize borated alkyl catechols wherein the catechol to boron mole ratio was either 3:2 or 1:1. The 3:2 catechol was prepared as in Example 4 above while the 1:1 catechol was also prepared in Example 4 above, but using an additional 44.5 g. of boric acid to achieve a 1:1 nitrogen to boron mole ratio. The results are shown in Table V below.

TABLE V
Ethylamines - Borate Stability and Viscosity[2]

| Example | Amine | Borate C:B[1] | Hydrolytic Stability Rating[3] | Visc.[2] cSt @ 100° C. |
|---|---|---|---|---|
| 35 | Triethyl | 3:2 | 6 | 310 |
| 36 | Triethyl | 1:1 | 4 | — |
| 37 | Diethyl | 3:2 | 6 | 275 |
| 38 | Diethyl | 1:1 | 6 | 2050 |

[1]Catechol to Boron mole ratio in preparing borate.
[2]Desirable viscosities are below 400 cSt.
[3]1 = Extensive, immediate hydrolysis.
2 = Some immediate hydrolysis.
3 = Hydrolysis within one day.
4 = Hydrolysis within one to three days.
5 = Hydrolysis within three to seven days.
6 = Stable to atmospheric moisture for at least seven days.

Referring to Table V, Examples 37 and 38 show that the use of diethylamine stabilizes the borated alkyl catechols regardless of whether the ratio of catechol to boron is 1:1 (Formula VI) or 3:2 (Formula V). Examples 35 and 36 show that the use of triethylamine stabilizes only the 3:2 product. The poor stabilization in Example 36 may be due to stearic effects since the 1:1 product (Formula VI) has the boron atoms closer together.

EXAMPLES 39-40

In these Examples, two different aromatic amines were used in an attempt to stabilize the 3:2 borated alkyl catechol prepared in accordance with Example 4 above. The results are shown on Table VI below.

TABLE VI

| Example | Amine | Borate C:B[1] | Hydrolytic Stability Rating[2] | Visc. cSt @ 100° C. |
|---|---|---|---|---|
| 39 | Aniline | 3:2 | 3 | Not determined |
| 40 | Benzyl Amine | 3:2 | 4 | Not determined |

[1]Cateohol to boric acid molar ratio in preparing borate.
[2]See Table V for rating.

Referring to Table VI, Examples 39 and 40 show that aniline and benzyl amine were not acceptable hydrolytic stabilizing agents for the borated alkyl catechols of this invention.

EXAMPLE 41

Preparation of Alpha-Olefin Oligomer Having a Number Average Carbon of 41

A sample of unhydrogenated $C_{30}$ to $C_{50}$ 1-decene oligomers was obtained using procedures essentially the same as those described in U.S. Pat. No. 4,045,507. The sample had a boiling point above 215° C. at 0.5 mm Hg and contains the following olefins, found using supercritical fluid chromatography: $C_{30}$, 14%; $C_{40}$, 64%; and $C_{50}$, 22% (carbon number average $C_{41}$). Analysis by NMR for olefin type showed 95% branched olefins.

EXAMPLE 42

Alkylation of Catechol with ($C_{30}$ to $C_{50}$) the Alpha Olefin Oligomer Mixture of Example 41

A mixture of catechol (19.3 g), the olefin mixture of Example 41 (100 g), and triflic acid (2 g) was heated while stirring for 6 hr at 140° C. The reaction mixture was cooled, taken up in n-hexane (200 ml), and extracted several times with 100 ml portions of aqueous 2-propanol (75/25) to remove the acid and any unreacted catechol. After drying over anhydrous sodium sulfate, the product was filtered and then stripped under high vacuum (about 0.5 mm Hg) at 120°–135° C. for 45 min. to give 111 g of dark amber alkylcatechol as an oil. This product gave a hydroxyl number of 105 mg KOH/g sample, which corresponded to about 65% yield based on the catechol.

EXAMPLE 43

Boration of Product of Example 42

A total of 105.6 g of the alkylcatechol prepared in Example 42 and boric acid (4.1 g) were reacted by heating, while stirring, at reflux in toluene (100 ml), and collecting the water of reaction in a Dean-Stark trap. After refluxing for 3 hours, a total of 3.0 g of water was recovered, although water formation stopped after 2 hours. Since no solids were visible, the reaction mixture was not filtered, and toluene was stripped to give about 106 g of borated alkylcatechol, which was fluid at room temperature. Exposure of a small sample of the purple borated alkylcatechol to atmospheric moisture led to formation of a boric acid crust on the surface of the sample, indicating that the boration reaction had occurred and the product was hydrolytically unstable.

EXAMPLE 44

Stabilization of Borated Alkylcatechol from Example 43 with Diethylamine

A sample (about 10 g) of the borated alkylcatechol prepared in Example 43 and maintained under nitrogen was dissolved in toluene (15 ml) to form a solution. This solution, while stirring, was treated with excess diethylamine (about 1.0 g) to form a reaction mixture. The reaction mixture was first stirred at room temperature for about 0.5 hour, then at reflux for 1 hour. The solvent was stripped under high vacuum (about 0.5 mm Hg) by heating up to about 135° C. for 1 hour to afford the diethylamine-stabilized borated alkylcatechol (10.2 g), as an amber colored viscous oil. Exposure of this diethylamine-stabilized product to atmospheric moisture showed no haze or precipitate after standing uncovered in a petri dish exposed to air for eight days.

Bench Test Oxidation Results

A series of runs were carried out in an oxidation bench test on fuly-formulated lubricating oils containing 1% of the additives prepared in Examples 43 and 44; 3.5% dispersant; 50 mmol/kg calcium as sulfonates; 17 mmol/kg zinc dialkyl dithiophosphate; and 6.8% viscosity index improver in Chevron 100N base oil. The oxidation test employed herein measures the resistance of the test sample to oxidation using pure oxygen with a Dornte-type oxygen abosrption apparatus as described in R. W. Dornte, "Oxidation of White Oils, " *Industrial and Engineering Chemistry,* 28, p. 26, (1936). The conditions used for the test are: an atmosphere of pure oxygen exposed to the test oil, an oil temperature of 340° F. (171° C.) and an oxidation catalyst comprised of metals, added as naphthenates, typically found in used oils from the Sequence IIIE engine test. The time required for 100 g of the test sample to absorb 1.0 L. of oxygen is measured. The results of the test are shown in Table VII.

TABLE VII

| | OXIDATION BENCH TEST RESULTS | | |
|---|---|---|---|
| Example | Additive | Hrs. to 1 L. Oxygen Uptake | Hrs. Improvement |
| 45 | None | 7.8 | Reference |
| 46 | 1% Alkyl-Catechol Borate from Example 43 | 11.8 | 4.0 |
| 47 | 1% Alkyl-Catechol Borate, Diethylamine-Stabilized from Example 44 | 10.8 | 3.0 |

The oxidation bench test results of Table VII show that both the borated and the amine-stabilized borated alkylcatechols are functioning as antioxidants when compared to a reference (Example 45). The slightly better antioxidancy of borated product (Example 46) over the amine-stabilized product (Example 47) may, in part, be attributed to the dilution effect of the boron level by the amine.

It is to be understood that various modifications of the present invention will occur to those skilled in the art upon reading the foregoing disclosure. It is intended that all such modifications be covered which reasonably fall within the scope of the appended claims. For example, it is within the purview of the present invention to use diethylamine to stabilize a borated alkyl catechol which has been partially stabilized with some other stabilizing agent such as a succinimide or, perhaps, another amine, such as triethylamine.

What is claimed is:

1. A composition comprising a complex of a borated alkyl catechol and an amount to hydrolytically stabilize the borated alkyl catechol of diethylamine wherein the borated alkyl catechol has a molar ratio of alkyl catechol to boron of 1:1 or 3:2 or mixtures thereof and further wherein the alkyl group of said borated alkyl catechol contains at least 10 carbon atoms.

2. A composition according to claim 1 wherein said alkyl group has from 32 to 60 carbon atoms.

3. A composition according to claim 1 wherein the amount of diethylamine is at least about 0.8 moles of diethylamine per mole of boron.

4. A composition according to claim 3 wherein the molar ratio of diethylamine to boron is about 0.8 to about 1.1.

5. The composition according to claim 2 wherein said alkyl group has from 36 to 50 carbon atoms.

6. The composition according to claim 1 wherein said alkyl group of said borated alkyl catechol is a mixture of alkyl groups having a number average carbon number of 35 to 45.

7. The composition according to claim 1 wherein said borated alkyl catechol is a mixture of (i) a borated alkyl catechol wherein the molar ratio of alkyl catechol to boron is 1:1 and (ii) an alkyl catechol wherein the molar ratio of alkyl catechol to boron is 3:2.

8. The composition according to claim 7 wherein said mixture consists essentially of borated alkyl catechol having an alkyl catechol to boron mole ratio of 3:2.

9. The composition according to claim 8 wherein said alkyl group of said borated alkyl catechol is a mixture of alkyl groups having a number average carbon number of 35 to 45.

10. The composition according to claim 9 wherein the molar ratio of diethylamine to boron is about 1:1.

11. The composition according to claim 4 wherein the alkyl catechol has from one to two alkyl groups and each alkyl group has from 32 to 60 carbon atoms.

12. A product prepared by a process which comprises: (1) forming a borated alkyl catechol wherein the borated alkyl catechol has a molar ratio of alkyl catechol to boron of 1:1 or 3:2 or mixtures thereof and further wherein the alkyl group of said borated alkyl catechol contains at least 10 carbon atoms; (2) contacting said borated alkyl catechol with diethylamine under conditions wherein a complex is formed between the diethylamine and the borated alkyl catechol, the amount of said diethylamine being sufficient to stabilize said borated alkyl catechol against hydrolysis.

13. A method to hydrolytically stabilize a borated alkyl catechol which comprises contacting said borated alkyl catechol with a hydrolytically stabilizing amount of diethylamine under conditions wherein a complex is formed between the diethylamine and said borated alkyl catechol wherein the borated alkyl catechol has a molar ratio of alkyl catechol to boron of 1:1 or 3:2 or mixtures thereof and further wherein the alkyl group of said borated alkyl catechol contains at least 10 carbon atoms.

14. A method according to claim 13 wherein the amount of diethylamine is such that the mole ratio of diethylamine to boron is about 0.8 to about 1.1.

15. A method according to claim 13 wherein said complex is formed in the presence of a solvent and a temperature of about 30° C. to about 100° C.

16. A method according to claim 13 wherein the alkyl group of said borated alkyl catechol contains from 32 to 60 carbon atoms.

17. A method according to claim 13 wherein wherein said alkyl group of said borated alkyl catechol is a mixture of alkyl groups having a number average carbon number of 35 to 45.

18. A lubricating oil composition comprising a major amount of an oil of lubricating viscosity and a minor amount of a hydrolytically stable diethylamine borated alkyl catechol complex wherein said complex is derived from a borated alkyl catechol having an alkyl group containing at least 10 carbon atoms and an alkyl catechol to boron ratio of 1:1 or 3:2 or mixtures thereof.

19. A lubricating oil composition of claim 18 wherein the amount of said complex is from 0.05% to 20% by weight of said composition.

20. A composition according to claim 19 wherein the amount of the diethylamine to the borated alkyl catechol ranges from 0.8 to 1.1 molar equivalents of diethylamine to one mole of boron.

21. A lubricating oil composition according to claim 20 wherein the alkyl group of said borated alkyl catechol has from 32 to 60 carbon atoms.

22. A lubricating oil composition according to claim 20 wherein the alkyl group of said borated alkyl catechol is a mixture of alkyl groups having a number average carbon number of 35 to 45.

23. A method for reducing oxidation and deposits during operation of an internal combustion engine comprising operating said internal combustion engine with a lubricating oil composition according to claim 18.

24. A composition comprising: (1) a complex of borated alkyl catechol and an amount of diethylamine to hydrolytically stabilize the borated alkyl catechol wherein the borated alkyl catechol has a molar ratio of alkyl catechol to boron of 1:1 or 3:2 or mixtures thereof and further wherein the alkyl group of said borated alkyl catechol contains from at least 10 carbon atoms; and (2) a neutral carrier oil; and wherein said composition, the weight percent of said complex is from 5 to 80 based on the weight of said carrier oil.

25. The composition according to claim 24 wherein the alkyl group of said borated alkyl catechol is a mixture of alkyl groups having a number average carbon number of 35 to 45.

26. The composition according to claim 24 wherein the alkyl group of said borated alkyl catechol has from 32 to 60 carbon atoms.

27. The composition according to claim 25 wherein said borated alkyl catechol consists essentially of a borated alkyl catechol having a catechol to boron mole ratio of 3:2.

* * * * *